United States Patent [19]

Boston

[11] Patent Number: 4,619,770
[45] Date of Patent: Oct. 28, 1986

[54] METHOD AND APPARATUS FOR RECOVERING A FLUID FROM A FILTER

[75] Inventor: Ernest B. Boston, Phillips, Tex.

[73] Assignee: Phillips Petroleum Company, Bartlesville, Okla.

[21] Appl. No.: 689,534

[22] Filed: Jan. 7, 1985

[51] Int. Cl.$^4$ ............................................. B01D 11/00
[52] U.S. Cl. .................................. 210/772; 210/797; 210/804; 210/805; 210/259; 210/296; 210/511
[58] Field of Search ............... 210/772, 797, 798, 799, 210/804, 805, 269, 275, 409, 412, 511, 259, 296

[56] References Cited

U.S. PATENT DOCUMENTS

| | | | |
|---|---|---|---|
| 3,352,765 | 11/1967 | Warner et al. | 203/70 |
| 3,417,103 | 12/1968 | Warner | 260/332.1 |
| 3,433,816 | 3/1969 | Muller | 210/772 |
| 3,450,262 | 6/1969 | Hirs | 210/772 |
| 3,912,664 | 10/1975 | Wainer | 260/2.3 |
| 4,250,032 | 2/1981 | Costa | 210/772 |
| 4,275,218 | 6/1981 | Huxley | 549/87 |
| 4,350,596 | 9/1982 | Kennedy, Jr. | 210/804 |
| 4,501,670 | 2/1985 | Tyson | 210/772 |

OTHER PUBLICATIONS

"Filtration", by George Dickey, Reinhold Pub. Co., New York, N.Y., 1961.

Primary Examiner—John Adee
Attorney, Agent, or Firm—William R. Sharp

[57] ABSTRACT

A method and apparatus for recovering a product fluid from a filter, wherein a wash fluid is passed through the filter so as to yield a mixture of product fluid and wash fluid. The mixture is then phase separated in a phase separator into a first phase substantially comprising product fluid, and a second phase substantially comprising wash fluid.

17 Claims, 1 Drawing Figure

METHOD AND APPARATUS FOR RECOVERING A FLUID FROM A FILTER

BACKGROUND OF THE INVENTION

This invention relates to a method for recovering a fluid from a filter. In another aspect, the invention relates to an apparatus for such recovery.

In various chemical processes, filters are sometimes employed at some point or points in the process which act to separate out certain unwanted materials in a mixture. Many times, however a fluid having significant value is trapped in the filter. This fluid might be a valuable process solvent, product intermediate, product, unconverted feed or the like. In addition, this fluid retained in the filter could create environmental problems in the disposal of the filter cake. One example of a process as mentioned above is sulfolane production, wherein a crude mixture including sulfolane is passed through a filter to filter out unwanted by-products, process catalysts, etc. However, in addition to unwanted materials, the filter may also trap some of the sulfolane therein. Sulfolane has significant economic value such that it would be desirable to recover trapped sulfolane from the filter.

SUMMARY OF THE INVENTION

It is, therefore, an object of the present invention to provide a method and apparatus for recovering a desired fluid from a filter.

The above object is realized in a method wherein the filter is washed by passing a wash fluid through the filter, the wash fluid and first desired fluid being substantially insoluble in each other and of different densities. A first mixture containing wash fluid and first fluid results from this washing. The first mixture is then phase separated in a phase separator into at least two phases, wherein a first phase substantially comprises first fluid, and wherein a second phase substantially comprises wash fluid.

In a preferred embodiment, at least a portion of the second phase is removed from the phase separator and used as wash fluid. A crude mixture of first fluid, at least one other fluid, and other components is fed into a separation zone which yields a bottom product mixture substantially comprising first fluid and the other components. The bottom product is passed through the filter to yield a relatively pure first fluid product, a portion of the first fluid being trapped in the filter. Much of this trapped first fluid is recovered from the filter as described above by washing the filter. Where sulfolane is the first fluid, the wash fluid may be an aliphatic hydrocarbon in the molecular weight range of about $C_5$ to about $C_{16}$, the one other fluid is water, and the other components include catalyst sludge.

In another aspect of the present invention, an apparatus includes a filter having a first fluid trapped therein and a means for passing a wash fluid through the filter. The wash fluid and first fluid are substantially insoluble in each other and are of different densities such that first fluid is displaced from said filter to yield a first mixture substantially comprising wash fluid and first fluid. The apparatus also includes a phase separator means for phase separating the first mixture into at least two phases wherein a first phase substantially comprises first fluid, and a second phase substantially comprises wash fluid.

According to the present invention, therefore, fluid trapped in a filter may be recovered. Recovery of such trapped fluid is important where the fluid is valuable or where such fluid could create environmental problems in filter cake disposal. The invention is particularly useful when the trapped fluid is relatively non-volatile, as in the case of sulfolane, making it difficult to remove the fluid from the filter by methods such as evaporation.

DESCRIPTION OF THE PREFERRED EMBODIMENTS

Figure 1:
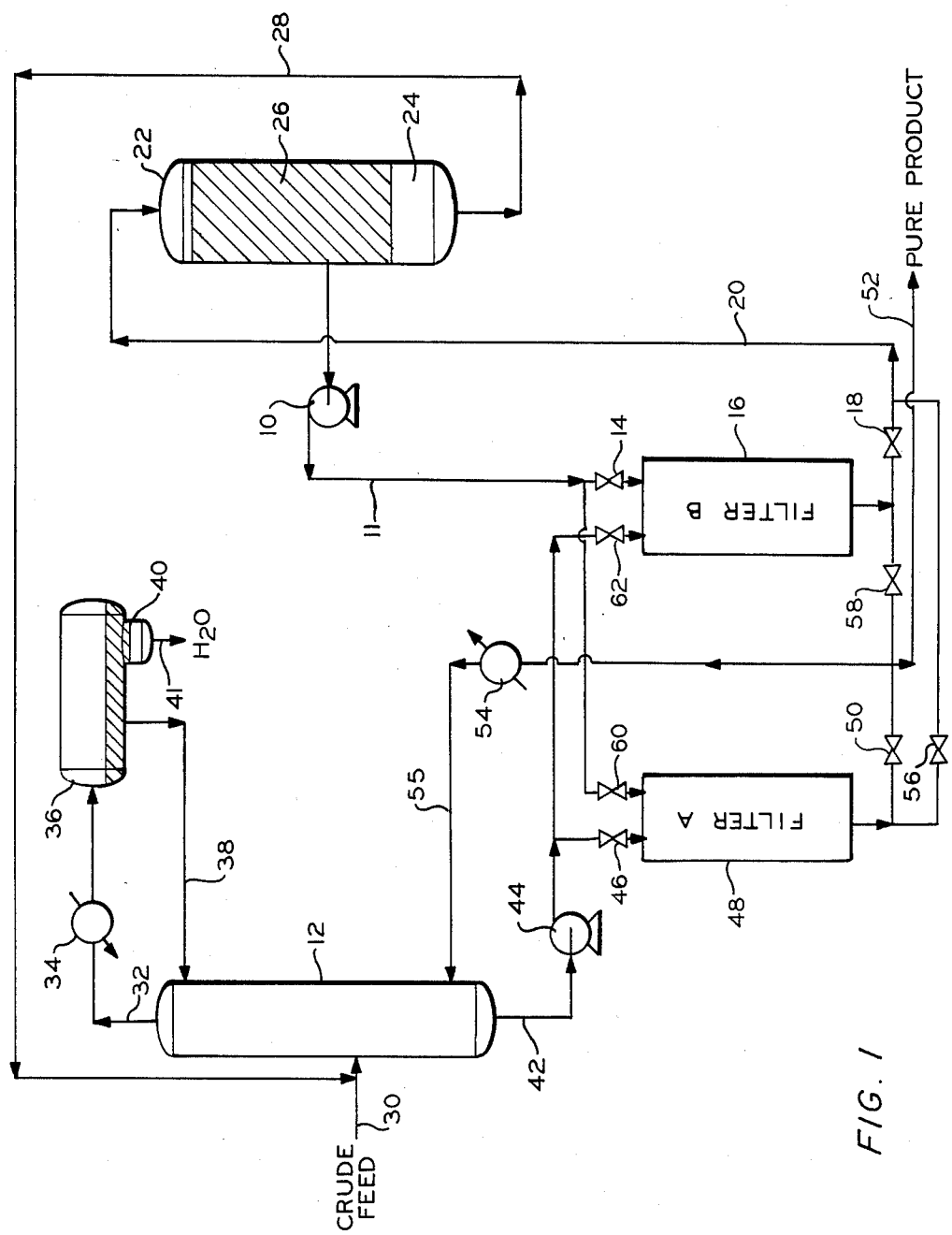
FIG. 1 is a schematic representation of one embodiment of an apparatus for performing the method according to the present invention.

A presently preferred embodiment of the present invention will now be described in terms of sulfolane production. It should be understood, however, that the present invention has application to other processes in which a desired fluid is trapped in a filter.

As used herein, sufolane compounds are saturated five-membered rings of four carbon atoms and a sulfur atom, the latter having two oxygen atoms directly attached thereto. Sulfolane compounds are useful as selective solvents, as intermediates in the production of various organic chemicals, and in pesticidal compositions. The term sulfolene compound as employed herein defines generically the unsubstituted and substituted unsaturated compounds comprising or containing a sulfolene nucleus, i.e., a five-membered ring of four carbon atoms and a sulfur atom with a single olefinic linkage between two adjacent carbon atoms of said ring, and two oxygen atoms each of which is directly attached to said sulfur atom. Sulfolane compounds are generally prepared by reaction of sulfur dioxide with a conjugated diene to form a sulfolene compound which is then catalytically hydrogenated to form the sulfolane compound. Suitable catalysts include metal hydrogenation catalysts, such as those containing or consisting of nickel, cobalt, copper, platinum, etc.

Referring now to FIG. 1, a schematic representation of a sulfolane purification apparatus is shown. It should be understood that the various arrows shown represent conduits, which will hereinafter be referred to as "lines". The direction for each arrow indicates the direction of fluid flow. As shown, a crude mixture containing the product sulfolane is fed into line 30. The crude feed typically comprises sulfolane, sulfolene, water, and catalyst sludge. This crude feed mixture is made as generally described above. More specifically, a particular method and apparatus for production of such a mixture is disclosed in U.S. Pat. No. 3,417,103 of Warner, whose disclosure is herein incorporated by reference. The apparatus of FIG. 1 serves to purify this crude feed to yield a substantially pure sulfolane product.

The apparatus shown in FIG. 1 includes a fractionator 12 which receives the crude feed; filters A and B denoted by reference characters 48 and 16 respectively; phase separator tank 22; condensor 34; valves 14, 18, 46, 50, 56, 58, 60, and 62; accumulator 36; and reboiler 54. As to the filters, any type of closed filter may be used such as horizontal or vertical leaf, cartridge, plate-and-frame, rotary precoat and the like. The illustrated embodiment employs two filters so that one filter may be on stream while the other filter is being washed. It should be understood, however, that only one filter could be employed providing some valve means is provided to allow only one of on stream flow or wash flow at any one time. The above-mentioned valves serve this purpose for the filters in the illustrated embodiment. In addition, although an external reboiler and an associated pump is employed in the FIG. 1 apparatus, an internal (in fractionator 12) reboiler or thermosyphon reboiler could be used.

The apparatus of FIG. 1 may be operated as follows. It will be assumed in this discussion that filter 48 is on stream (in on stream mode) and filter 16 is being washed (in wash mode). Accordingly, valves 14, 18, 46, and 50 are open, whereas valves 56, 58, 60, and 62 are closed for this mode of operation.

A wash fluid is pumped by pump 10 through line 11. The source of this wash fluid will be discussed in further detail below. The wash fluid then passes through valve 14, and through filter 16. The wash fluid displaces sulfolane fluid trapped within filter 16. The sulfolane trapped in filter 16 derives from the prior use of filter 16 in the on stream mode. This mode will be discussed in regard to the other filter. Was fluid passing through filter 16 displaces sulfolane trapped therein to yield a mixture substantially comprising sulfolane and wash fluid, which is passed through open valve 18. The catalyst sludge typically remains in filter 16 after this washing occurs. The mixture of wash fluid and sulfolane then passes through line 20 into phase separator 22. The wash fluid and sulfolane should be mutually insoluble in each other and of different densities so that phase separation can occur accordingly in phase separator 22. In the illustrated embodiment, the wash fluid may be any aliphatic hydrocarbon in the molecular weight range of about $C_5$ to about $C_{16}$. Suitable hydrocarbon wash fluids include isooctane, iosheptane, and cyclohexane. It is emphasized, however, that any wash fluid which is insoluble in sulfolane and of a different density than sulfolane would be suitable according to the present invention.

It should also be noted that it is desirable to utilize buoyancy to aid in displacement of sulfolane from the filter. For example, in FIG. 1, downflow of wash fluid through the filter is indicated since the preferred hydrocarbon wash fluid is lighter than sulfolane. If the opposite was the case, upflow through the filter would be preferred.

Phase separator 22 is typically operated at around ambient temperature. It is desirable to operate phase separator 22 at such low temperatures, since at relatively high temperatures the wash fluid and the sulfolane may tend to dissolve in each other to an undesirable degree. The mixture received by phase separator 22 is separated into two phases. A first phase indicated at 24 substantially comprises sulfolane, and a second phase 26 comprises wash fluid. Although the wash fluid and sulfolane are relatively insoluble in each other, some wash fluid will dissolve in the sulfolane. Therefore, first phase 24 comprises sulfolane with a very small amount of wash fluid dissolved therein.

At least a portion of the second phase comprising wash fluid is removed by pump 10 and fed through line 12 in order to wash filter 16. Therefore, a continuous washing cycle is provided.

At least a portion of the first phase 24 which, as noted above, substantially comprises a solution of sulfolane and wash fluid, is passed through line 28 and into fractionator 12. The crude feed mixture, discussed above, is also fed into fractionator 12 via line 30. Fractionator 12 is typically operated at a nominal temperature of about 250° F., but the kettle temperature will be somewhat higher, 280 to about 330° F., depending on column bottom pressure and the water concentration desired in the kettle product. Fractionation of the received fluids takes place accordingly in fractionator 12 to yield a distillate which substantially comprises water and wash fluid vapor. This distillate is passed through line 32, and into condensor 34. Condensor 34 acts to cool the distillate in a conventional manner so as to yield a condensate which is received by accumulator 36. Hydrocarbon wash fluid and water in the received mixture tend to separate in accumulator 36 such that a top phase of wash fluid and a bottom phase of water results. In the illustrated embodiment, the top phase of wash fluid is fed back into fractionator 12 as reflux in a conventional manner via line 38. As shown, a bottom phase of primarily water is preferably collected in water leg 40, and can be withdrawn therefrom by means of line 41. The water leg permits removal of the water from accumulator 36 without inadvertent entrainment of wash fluid. By phase separating the wash fluid from the water, the water may be conveniently disposed without risk of causing environmental problems. In addition, it should be noted that for the above mentioned separation to be accomplished, it is preferable that the water and wash fluid are mutually insoluble, and that the wash fluid has a higher volatility than sulfolane. Any noncondensibles, if present, can be vented from accumulator 36 by means not shown.

Fractionator 12 also yields a bottom product, or residue, which substantially comprises sulfolane, catalyst sludge, and small amounts of sulfolene. This bottom product is removed from fractionator 12 via line 42 by pump 44. The bottom product mixture is then passed through valve 46 and into filter 48. As the bottom product mixture passes through filter 48, substantially all of the catalyst sludge is filtered out. Additionally, a portion of the sulfolane is trapped within filter 48. This trapped sulfolane is washed from the filter substantially as described above in the wash mode. Filter 48 yields a relatively pure product which flows through valve 50 and into line 52. A portion of this product is drawn off as shown as pure product which substantially comprises only sulfolane, with very small amounts of sulfolene, $H_2O$, and essentially no catalyst sludge. Typically, this pure product will contain above about 90% sulfolane. A portion of the product fluid flows through reboiler 54 via line 52. Reboiler 54 heats fluid therein which is fed back into fractionator 12 via line 55.

Fractionator 12, condensor 34, accumulator 36, reboiler 54 and pump 44, therefore, comprise a distillation apparatus which can be considered a separation zone in which water (and trace amounts of wash fluid) is separated from the crude mixture. This zone might employ any suitable separation process such as liquid-liquid extraction, extractive distillation, crystallization or a combination of separation steps.

After filter 48 is maintained in the on stream mode for a predetermined length of time, filter 48 is then switched to the wash mode. Accordingly, filter 16 is switched to the on stream mode. In this mode of operation, valves 56, 58, 60, 62 are open, and valves 14, 18, 46 and 50 are closed. After the wash step with either filter, the filter may be drained and purged with an inert gas and or steamed to vaporize the wash fluid. This vaporized wash fluid may then be condensed and recovered, if desired.

A calculated example will now be given to further illustrate the invention, but should not be interpreted to limit the scope of the invention in any manner. The fractionator 12 is operated at 250° F. and atmospheric pressure. The phase separator 22 is operated at ambient temperature. The following table gives wt. % composition data of streams in certain lines wherein a nickel catalyst and isooctane wash fluid are employed.

| Line # | Sulfolane | Sulfolene | $H_2O$ | Ni Sludge | HC Wash |
|---|---|---|---|---|---|
| 30 | 60–65 | 0–2 | 35–40 | 1–2 | — |
| 41 | .3–.5 | Trace | 99.5–99.7 | — | Trace |
| 52 | 95–97 | .1–.3 | 3–5 | Trace | — |
| 28 | 95–97 | .1–.3 | 3–5 | Trace | Trace |

Obviously many modifications and variations of the present invention are possible in light of the above teachings. It is therefore understood that within the scope of the appended claims the invention may be practiced otherwise than as specifically described.

What is claimed is:

1. A method of recovering a first fluid, comprising sulfolane, from a filter in which it is trapped as a filtrate, comprising the steps of:
   (a) washing the filter by passing an aliphatic hydrocarbon wash fluid in the molecular weight range of about $C_5$ to about $C_{16}$ through the filter, the wash fluid and first fluid being substantially insoluble in each other and of different densities, wherein a first mixture containing wash fluid and first fluid results from said washing; and
   (b) phase separating the first mixture into at least two phases in a phase separator, wherein a first phase substantially comprises first fluid, and wherein a second phase substantially comprises wash fluid.

2. A method as recited in claim 1, further comprising the step (c) of removing at least a portion of the second phase from the phase separator and using at least a portion of the removed second phase as wash fluid in step (a).

3. A method as recited in claim 2, further comprising the step of removing at least a portion of the first phase from the phase separator.

4. A method as recited in claim 3, further comprising the step (d) of passing a second mixture through the filter before or after step (a), the second mixture containing first fluid wherein a portion of first fluid flowing through the filter is trapped in the filter, and wherein a product containing first fluid is produced after passing the second mixture through the filter.

5. A method as recited in claim 4, further comprising the step (e) of introducing a third mixture to a separation zone wherein the third mixture contains first fluid, at least one other fluid, and other components; and (f) separating the at least one other fluid from the third mixture in the separation zone to yield the second mixture.

6. A method as recited in claim 5, further comprising the step of introducing at least a portion of the removed first phase to the separation zone.

7. A method as recited in claim 6, wherein said step (f) includes the step of fractionating the third mixture said fractionating yielding a bottom product substantially comprising first fluid and the other components.

8. A method as recited in claim 7, wherein the bottom product is used as the second mixture passed through the filter.

9. A method as recited in claim 1, wherein the wash fluid is isoheptane.

10. A method as recited in claim 1, wherein the wash fluid is isooctane.

11. A method as recited in claim 8, wherein at the least one other fluid is water.

12. A method as recited in claim 11, wherein said other components include catalyst sludge.

13. An apparatus comprising:
   a filter;
   means for passing a wash fluid through said filter, wherein any of a first fluid trapped in said filter is displaced from said filter to yield a first mixture substantially comprising wash fluid and first fluid;
   phase separator means for phase separating the first mixture into at least two phases, a first phase substantially comprising first fluid, and a second phase substantially comprising wash fluid;
   means for passing a second mixture, which includes first fluid, through said filter;
   valve means for allowing only one of said second mixture and said wash fluid to be passed through said filter at any one time;
   second separator means for receiving a third mixture which includes first fluid and at least one other fluid, said second separator means being capable of separating said at least one other fluid from the third mixture to yield the second mixture.

14. An apparatus as recited in claim 13, wherein said means for passing a wash fluid acts to remove at least a portion of the second phase from said phase separator means, the removed second phase being passed through said filter.

15. An apparatus as recited in claim 14, further comprising a means for removing at least a portion of the first phase from said phase separator means.

16. An apparatus as recited in claim 15, further comprising a means for introducing at least a portion of the first phase removed from said phase separator means to said second separator means.

17. An apparatus as recited in claim 16, wherein said second separator means includes a fractionator to which the third mixture and removed first phase is introduced, said fractionator yielding a bottom product as the second mixture.

* * * * *